(12) United States Patent
Campbell et al.

(10) Patent No.: US 8,280,172 B1
(45) Date of Patent: Oct. 2, 2012

(54) EDGE LOCATION MEASUREMENT CORRECTION FOR COAXIAL LIGHT IMAGES

(75) Inventors: Shannon Roy Campbell, Woodinville, WA (US); Mark Lawrence Delaney, Shoreline, WA (US)

(73) Assignee: Mitutoyo Corporation, Kawasaki-shi (JP)

( * ) Notice: Subject to any disclaimer, the term of this patent is extended or adjusted under 35 U.S.C. 154(b) by 0 days.

(21) Appl. No.: 13/053,880

(22) Filed: Mar. 22, 2011

(51) Int. Cl.
*G06K 9/48* (2006.01)
(52) U.S. Cl. ........... 382/199; 382/152; 382/100; 348/86
(58) Field of Classification Search ................. 382/100, 382/152, 199; 348/86
See application file for complete search history.

(56) References Cited

U.S. PATENT DOCUMENTS

| | | | |
|---|---|---|---|
| 4,670,659 A | 6/1987 | Loose | |
| 4,744,663 A | 5/1988 | Hamashima | |
| 5,563,702 A | 10/1996 | Emery | |
| 5,822,055 A | 10/1998 | Tsai | |
| 6,323,953 B1 | 11/2001 | Blaesing-Bangert | |
| 6,542,180 B1 | 4/2003 | Wasserman | |
| 6,621,928 B1* | 9/2003 | Inagaki et al. | 382/199 |
| 6,836,560 B2 | 12/2004 | Emery | |
| 7,324,682 B2 | 1/2008 | Wasserman | |
| 7,454,053 B2* | 11/2008 | Bryll et al. | 382/152 |
| 7,570,795 B2* | 8/2009 | Yu et al. | 382/141 |
| 7,724,942 B2* | 5/2010 | Bryll | 382/151 |
| 7,899,239 B2* | 3/2011 | Nishimaki et al. | 382/145 |
| 8,045,002 B2* | 10/2011 | Gladnick et al. | 348/132 |
| 2005/0213807 A1* | 9/2005 | Wasserman | 382/152 |
| 2006/0093205 A1* | 5/2006 | Bryll et al. | 382/152 |
| 2007/0112535 A1 | 5/2007 | Bryll | |
| 2010/0158343 A1 | 6/2010 | Bryll | |

OTHER PUBLICATIONS

Campbell, S.R., "Autofocus Video Tool and Method for Precise Dimensional Inspection," U.S. Appl. No. 12/608,943, filed Oct. 29, 2009.
Fu, J., and R. Hocken, "Thickness Correction for Edge Detection of Optical Coordinate Measuring Machines," Proceedings of the American Society for Precision Engineering (ASPE), Monterey, California, Oct. 31-Nov. 5, 1999, 4 pages.
"QVPAK 3D CNC Vision Measuring Machine: Operation Guide," Version 2.0, Manual No. 4911GB, Series No. 359, Mitutoyo Corporation & Micro Encoder Inc., Kanagawa, Japan, Sep. 1996, 86 pages.
"QVPAK 3D CNC Vision Measuring Machine: User's Guide," Version 7.1, 2d ed., Manual No. 99MCB225A, Series No. 359, Mitutoyo Corporation & Micro Encoder Inc., Kanagawa, Japan, Sep. 2003, 370 pages.
Extended European Search Report mailed Jun. 20, 2012, in European Application No. 12160842.6, filed Mar. 22, 2011, 6 pages.

* cited by examiner

*Primary Examiner* — Samir Ahmed
(74) *Attorney, Agent, or Firm* — Christensen O'Connor Johnson Kindness PLLC

(57) ABSTRACT

A method for correcting coaxial light image edge location errors in a precision machine vision inspection system is disclosed. The method comprises comparing an edge position measurement of a workpiece edge feature using coaxial light and stage light. Edge position measurements using stage light have a lower uncertainty than that of coaxial light. Position correction factors may be determined from the difference between the two edge position measurements. The position correction factors may be stored for correcting subsequent edge position measurements that are based on images acquired using coaxial light. In some embodiments, position correction factors may be determined based on comparing edge position measurements for a plurality of edges.

11 Claims, 5 Drawing Sheets

US 8,280,172 B1

EDGE LOCATION MEASUREMENT CORRECTION FOR COAXIAL LIGHT IMAGES

FIELD OF THE INVENTION

The invention relates generally to machine vision inspection systems, and more particularly to methods of correcting illumination-dependent errors in edge location measurements.

BACKGROUND

Precision machine vision inspection systems (or "vision systems" for short) can be utilized to obtain precise dimensional measurements of inspected objects and to inspect various other object characteristics. Such systems may include a computer, a camera and optical system, and a precision stage that is movable in multiple directions so as to allow the camera to scan the features of a workpiece that is being inspected. One exemplary prior art system that is commercially available is the QUICK VISION® series of PC-based vision systems and QVPAK® software available from Mitutoyo America Corporation (MAC), located in Aurora, Ill. The features and operation of the QUICK VISION® series of vision systems and the QVPAK® software are generally described, for example, in the *QVPAK 3D CNC Vision Measuring Machine User's Guide*, published January 2003, and the *QVPAK 3D CNC Vision Measuring Machine Operation Guide*, published September 1996, each of which is hereby incorporated by reference in their entirety. This product, as exemplified by the QV-302 Pro model, for example, is able to use a microscope-type optical system to provide images of a workpiece at various magnifications, and move the stage as necessary to traverse the workpiece surface beyond the limits of any single video image. A single video image typically encompasses only a portion of the workpiece being observed or inspected, given the desired magnification, measurement resolution, and physical size limitations of such systems.

Machine vision inspection systems generally utilize automated video inspection. U.S. Pat. No. 6,542,180 (the '180 patent) teaches various aspects of such automated video inspection and is incorporated herein by reference in its entirety. As taught in the '180 patent, automated video inspection metrology instruments generally have a programming capability that allows an automatic inspection event sequence to be defined by the user for each particular workpiece configuration. This can be implemented by text-based programming, for example, or through a recording mode which progressively "learns" the inspection event sequence by storing a sequence of machine control instructions corresponding to a sequence of inspection operations performed by a user with the aid of a graphical user interface, or through a combination of both methods. Such a recording mode is often referred to as "learn mode" or "training mode." Once the inspection event sequence is defined in "learn mode," such a sequence can then be used to automatically acquire (and additionally analyze or inspect) images of a workpiece during "run mode."

The machine control instructions including the specific inspection event sequence (i.e., how to acquire each image and how to analyze/inspect each acquired image) are generally stored as a "part program" or "workpiece program" that is specific to the particular workpiece configuration. For example, a part program defines how to acquire each image, such as how to position the camera relative to the workpiece, at what lighting level, at what magnification level, etc. Further, the part program defines how to analyze/inspect an acquired image, for example, by using one or more video tools such as edge/boundary detection video tools.

Video tools (or "tools" for short) and other graphical user interface features may be used manually to accomplish manual inspection and/or machine control operations (in "manual mode"). Their set-up parameters and operation can also be recorded during learn mode, in order to create automatic inspection programs, or "part programs." Video tools may include, for example, edge/boundary detection tools, autofocus tools, shape or pattern-matching tools, dimension-measuring tools, and the like.

Machine vision inspection systems may illuminate a workpiece edge feature using various types of illumination. For example, stage light and coaxial light are discussed in the '180 patent. High resolution edge location measurements may return different results depending on the type of illumination used when acquiring an image that is used for edge location. Various methods are known in the art for correcting the different results of edge location measurements obtained using different types of illumination. For example, a publication by Fu et al. (*Thickness Correction for Edge Detection of Optical Coordinate Measuring Machines*, ASPE Proceedings, Oct. 31-Nov. 5, 1999, Monterey Calif.) describes various methods for compensating for errors associated with such measurements. However, the methods employed therein are impractical for a number of applications. For example, they are time consuming, may require a special reference object to measure, and may be too complex for implementation by a relatively unsophisticated user of a machine vision inspection system. Additionally the methods address errors which arise from thickness of an edge feature and do not provide adequate high accuracy compensation/correction directed to the variety of edge conditions and workpiece materials encountered by a general purpose machine vision inspection system. Improvements in methods for correcting edge location results such that they are consistent and accurate, regardless of the type of illumination used for image acquisition, would be desirable.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter. The terms edge location and edge position are generally used interchangeably herein.

A method is provided for correcting edge location results such that they are consistent and accurate for types of illumination that may otherwise cause a shift in an imaged edge position (e.g., an offset or bias) when used to illuminate an image of the edge. In particular, it has been found that certain machine vision inspection systems may be designed such that its stage light provides relatively ideal (e.g., consistent and accurate) imaged edge positions. However, in contrast, it has been found that coaxial light provides an offset or bias in imaged edge positions. Therefore, briefly stated, in various embodiments, a method according to this invention establishes a reference measurement of an edge based on a "stage light image"; establishes a "coaxial light measurement" of the same edge in a "coaxial light image"; determines a difference between the coaxial light measurement and the stage light reference measurement; and corrects subsequent edge location measurements in coaxial light images based on that difference. Such a method has been found to be both simpler and more accurate in certain vision systems than previously known methods of correcting illumination-dependent edge location errors. In addition, the method may be implemented without the need for a precisely fabricated reference object. In some embodiments, such a method may be implemented as a generic illumination-dependent correction for the machine vision inspection system. In some embodiments, such a method may be implemented for a specific workpiece type or a specific workpiece edge, based on learn mode operations that use a representative workpiece to establish a workpiece-specific or edge-specific illumination-dependent correction applicable to coaxial light measurements on subsequent similar workpieces and/or edges.

In various embodiments, the machine vision inspection system comprises an imaging system, a workpiece stage, a coaxial illumination portion which projects coaxial light from an objective lens of the imaging system toward the workpiece stage, a stage light illumination portion which projects stage light from the workpiece stage toward the imaging system, and a control system. In some embodiments, the stage light comprises a light generator and collimating optics that output collimated stage source light. In some embodiments, the stage light also comprises an output light diffuser that inputs collimated light and outputs stage source light that is at least partially diffuse. The method comprises the steps of: (a) positioning a workpiece on the workpiece stage with an edge feature of the workpiece in a field of view of the imaging system, wherein the edge feature comprises a boundary between a region which reflects coaxial light to the imaging system and a region which transmits stage light to the imaging system; (b) holding the edge feature steady at a first position in the field of view and acquiring a first image of the edge using one of the coaxial light and the stage light; (c) holding the edge feature steady at the first position in the field of view and acquiring a second image of the edge using the other of the coaxial light and the stage light; (d) determining a first edge position measurement for a defined portion of the edge feature in the first image; (e) determining a second edge position measurement for the defined portion of the edge feature in the second image; (f) determining a coaxial light edge position correction factor based on a difference between the first edge position measurement and the second edge position measurement; and (g) storing the coaxial light edge position correction factor for correcting subsequent edge position measurements that are based on images acquired using coaxial light.

In some embodiments, the method may further comprise acquiring a subsequent image of an edge feature using the coaxial light; determining an edge position measurement for the edge feature in the subsequent image; and correcting that edge position measurements by adjusting it based on the coaxial light edge position correction factor.

In some embodiments, the method may further comprise performing the steps (a) through (e) a plurality of times, wherein the edge position correction factor is determined in step (f) based on the resulting plurality of first and second edge position measurements. In some embodiments, the steps (a) through (e) are performed a plurality of times using a single edge. In some embodiments, the steps (a) through (e) are performed a plurality of times using a plurality of edges.

In some embodiments, the coaxial light edge position correction factor stored in step (g) is used to correct coaxial light image edge locations measured during run mode operations on various workpieces. In some embodiments, the steps (a) through (g) may be performed in association with a learn mode of a machine vision inspection system using a representative workpiece, such that the coaxial light edge position correction factor is customized for a particular type of workpiece and/or a particular type of edge configuration and/or material on that workpiece.

In some embodiments, the method may be applied based on a user selection in a graphical user interface (GUI) of the machine vision inspection system. In some embodiments, the GUI may include an illumination-dependent correction selector that governs whether to apply the correction method globally, and/or for a particular measurement, etc.

We may define "offset error" to mean an edge location error that has a relatively consistent magnitude, and a consistent polarity relative to the light/dark polarity of an edge that is measured. For some precision machine vision inspection systems (e.g., the QUICK VISION® series referred to previously), an uncorrected edge position measurement using coaxial illumination may have an offset error which is on the order of one pixel unit on the imaging detector, or less (e.g., a sub-pixel error). For various lenses and magnifications this may correspond to a measurement error of a few microns (e.g., corresponding to half a pixel unit), or less. However, using a coaxial light edge position correction factor to correct an edge position measurement as disclosed herein may significantly reduce this offset error (e.g., by a factor of 2-5, or more) such that the coaxial light measurement accuracy approaches the range of manufacturing tolerances of precision reference objects (e.g., on the order of a few tenths of a micron), without actually using such a precision reference object.

It should be appreciated that the methods disclosed herein for determining and applying coaxial light edge position correction factors may provide correction of coaxial light image offset errors with sub-pixel resolution and accuracy in a manner that is easily implemented by an unskilled user of a precision machine vision inspection system, and without the use of a precision reference object. These features are particularly valued by certain users of precision machine vision inspection systems.

DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION

Figure 1:
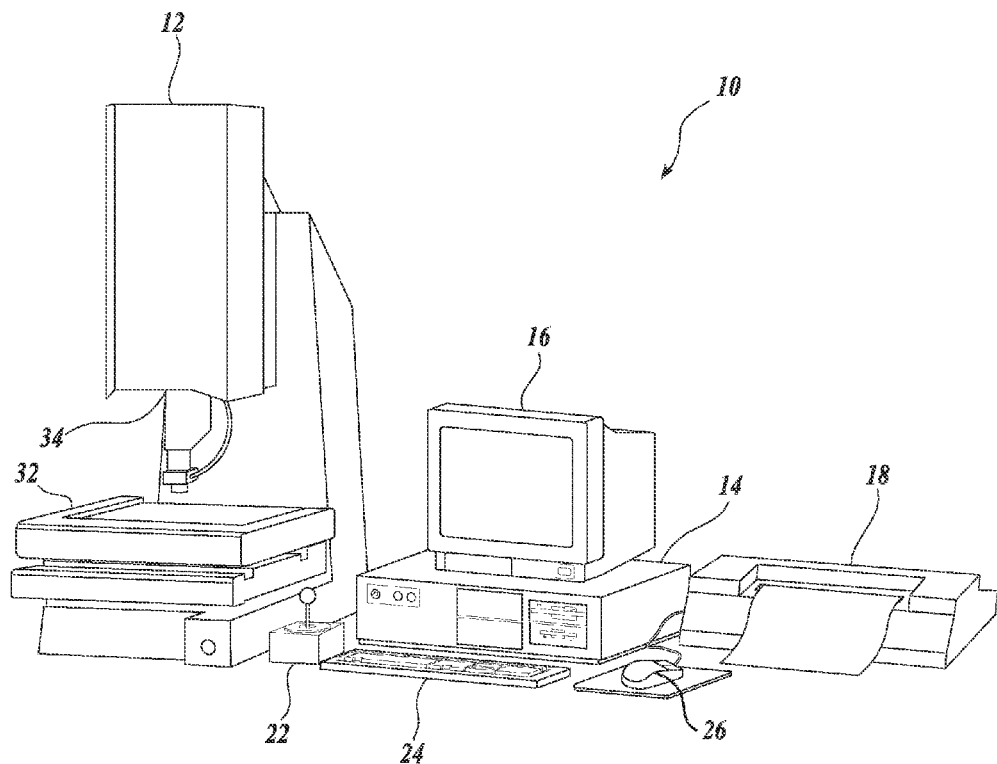
FIG. 1 is a diagram showing various typical components of a general purpose precision machine vision inspection system.

FIG. 1 is a block diagram of one exemplary machine vision inspection system 10 usable in accordance with methods described herein. The machine vision inspection system 10 includes a vision measuring machine 12 that is operably connected to exchange data and control signals with a controlling computer system 14. The controlling computer system 14 is further operably connected to exchange data and control signals with a monitor or display 16, a printer 18, a joystick 22, a keyboard 24, and a mouse 26. The monitor or display 16 may display a user interface suitable for controlling and/or programming the operations of the machine vision inspection system 10.

The vision measuring machine 12 includes a moveable workpiece stage 32 and an optical imaging system 34 which may include a zoom lens or interchangeable lenses. The zoom lens or interchangeable lenses generally provide various magnifications for the images provided by the optical imaging system 34. The machine vision inspection system 10 is generally comparable to the QUICK VISION® series of vision systems and the QVPAK® software discussed above, and similar state-of-the-art commercially available precision machine vision inspection systems. The machine vision inspection system 10 is also described in commonly assigned U.S. Pat. Nos. 7,454,053, 7,324,682, 8,111,938 and 8,111,905, which are each incorporated herein by reference in their entireties.

Figure 2:
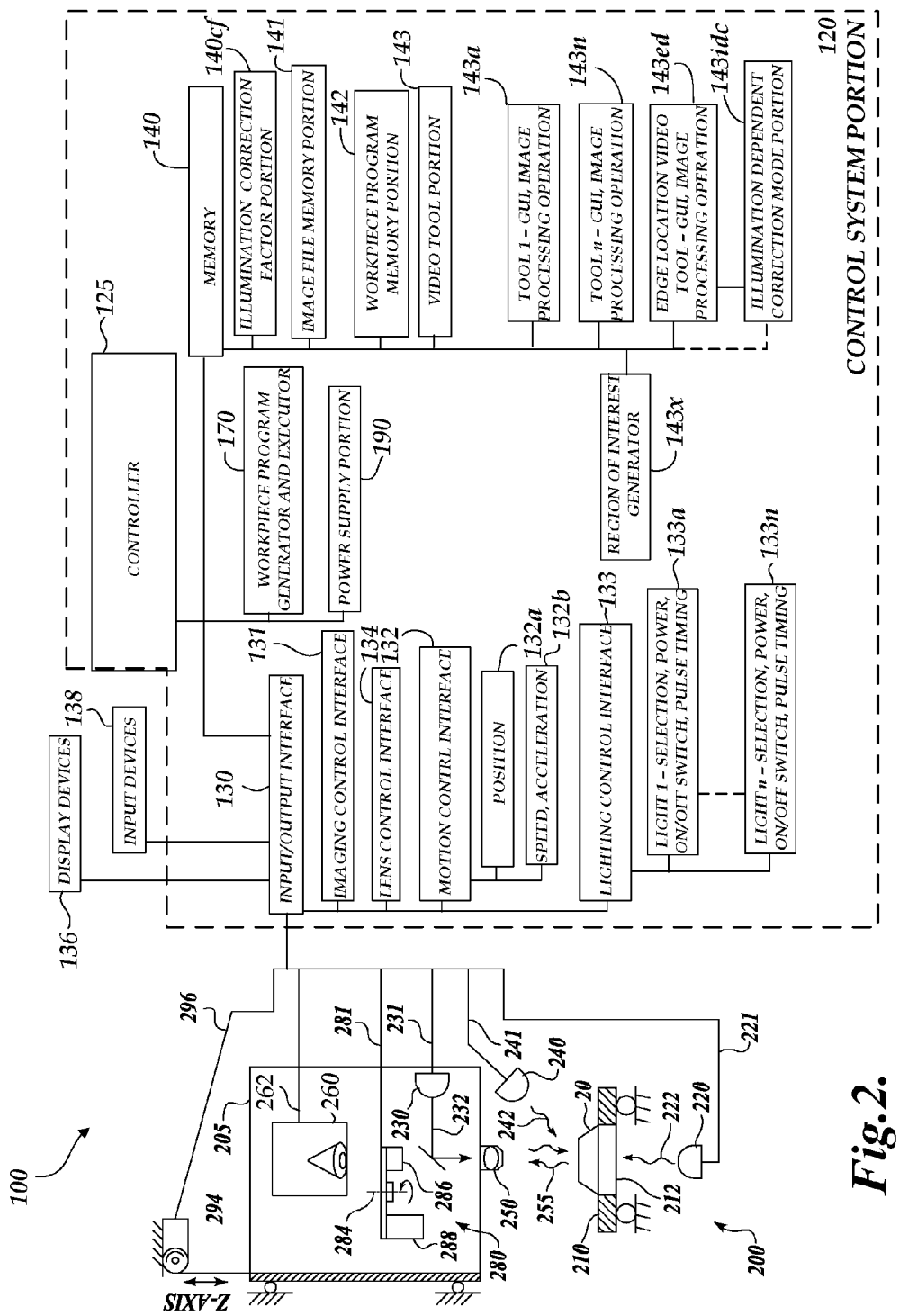
FIG. 2 is a block diagram of a control system portion and a vision components portion of one embodiment of the machine vision inspection system of FIG. 1, including features disclosed herein.

FIG. 2 is a block diagram of a control system portion 120 and a vision components portion 200 of one embodiment of a machine vision inspection system 100 including features disclosed herein. As will be described in more detail below, the control system portion 120 is utilized to control the vision components portion 200. The vision components portion 200 includes an optical assembly portion 205, light sources 220, 230, and 240, and a workpiece stage 210 having a central transparent portion 212. The workpiece stage 210 is controllably movable along X and Y axes that lie in a plane that is generally parallel to the surface of the stage where a workpiece 20 may be positioned. The optical assembly portion 205 includes a camera system 260, an interchangeable objective lens 250, and may include a turret lens assembly 280 having lenses 286 and 288. Alternatively to the turret lens assembly, a fixed or manually interchangeable magnification-altering lens, or a zoom lens configuration, or the like, may be included. The optical assembly portion 205 is controllably movable along a Z-axis that is generally orthogonal to the X and Y axes, by using a controllable motor 294, as described further below.

A workpiece 20, or a tray or fixture holding a plurality of workpieces 20, which is to be imaged using the machine vision inspection system 100 is placed on the workpiece stage 210. The workpiece stage 210 may be controlled to move relative to the optical assembly portion 205, such that the interchangeable objective lens 250 moves between locations on a workpiece 20, and/or among a plurality of workpieces 20. One or more of a stage light 220, a coaxial light 230, and a surface light 240 may emit source lights 222, 232, or 242, respectively, to illuminate the workpiece or workpieces 20. The source light is reflected or transmitted as workpiece light 255, which passes through the interchangeable objective lens 250 and the turret lens assembly 280 and is gathered by the camera system 260. The image of the workpiece(s) 20, captured by the camera system 260, is output on a signal line 262 to the control system portion 120. The light sources 220, 230, and 240 may be connected to the control system portion 120 through signal lines or busses 221, 231, and 241, respectively. To alter the image magnification, the control system portion 120 may rotate the turret lens assembly 280 along axis 284 to select a turret lens, through a signal line or bus 281.

In various exemplary embodiments, the optical assembly portion 205 is movable in the vertical Z-axis direction relative to the workpiece stage 210 using a controllable motor 294 that drives an actuator, a connecting cable, or the like, to move the optical assembly portion 205 along the Z-axis to change the focus of the image of the workpiece 20 captured by the camera system 260. The term Z-axis, as used herein, refers to the axis that is intended to be used for focusing the image obtained by the optical assembly portion 205. The controllable motor 294, when used, is connected to the input/output interface 130 via a signal line 296.

As shown in FIG. 2, in various exemplary embodiments, the control system portion 120 includes a controller 125, the input/output interface 130, a memory 140, a workpiece program generator and executor 170, and a power supply portion 190. Each of these components, as well as the additional components described below, may be interconnected by one or more data/control buses and/or application programming interfaces, or by direct connections between the various elements.

The input/output interface 130 includes an imaging control interface 131, a motion control interface 132, a lighting control interface 133, and a lens control interface 134. The motion control interface 132 may include a position control element 132a, and a speed/acceleration control element 132b. However, it should be appreciated that in various exemplary embodiments, such elements may be merged and/or indistinguishable. The lighting control interface 133 includes lighting control elements 133a-133n, which control, for example, the selection, power, on/off switch, and strobe pulse timing if applicable, for the various corresponding light sources of the machine vision inspection system 100.

The memory 140 includes an image file memory portion 141, a workpiece program memory portion 142 that may include one or more part programs, or the like, and a video tool portion 143. The memory 140 may also include an illumination correction factor portion 140cf, which stores illumination-dependent edge position correction factors (e.g., coaxial light edge position correction factors), as described in greater detail below. The video tool portion 143 includes tool portion 143a and other similar tool portions (~143m), which determine the GUI, image processing operation, etc., for each of the corresponding tools. The video tool portion 143 also includes a region of interest generator 143x that supports automatic, semi-automatic and/or manual operations that define various ROIs that are operable in various video tools included in the video tool portion 143. One exemplary edge detection video tool is explicitly represented for convenience of description, an edge detection video tool 143ed. It should be appreciated that other video tools may include similar edge detection features and operations within their scope. The edge detection video tool 143ed may include an illumination-dependent correction mode portion 143idc, which applies illumination-dependent edge position correction factors (e.g., coaxial light edge position correction factors) to substantially reduce or eliminate illumination-dependent offset errors, as described in greater detail below. Therefore, in various embodiments, the illumination-dependent correction mode portion 143idc may be considered as part of each individual video tool, or as a general feature of the video tool portion 143 which is applicable to a variety of different video tools.

In general, the memory portion 140 stores data usable to operate the vision system components portion 200 to capture or acquire an image of the workpiece 20 such that the acquired image of the workpiece 20 has desired image characteristics. The memory portion 140 may also store inspection result data, may further store data usable to operate the machine vision inspection system 100 to perform various inspection and measurement operations on the acquired images (e.g., implemented, in part, as video tools), either manually or automatically, and to output the results through the input/output interface 130. The memory portion 140 may also contain data defining a graphical user interface operable through the input/output interface 130.

The signal lines or busses 221, 231, and 241 of the stage light 220, the coaxial light 230, and the surface light 240, respectively, are all connected to the input/output interface 130. The signal line 262 from the camera system 260 and the signal line 296 from the controllable motor 294 are connected to the input/output interface 130. In addition to carrying image data, the signal line 262 may carry a signal from the controller 125 that initiates image acquisition.

One or more display devices 136 (e.g., the display 16 of FIG. 1) and one or more input devices 138 (e.g., the joystick 22, keyboard 24, and mouse 26 of FIG. 1) can also be connected to the input/output interface 130. The display devices 136 and input devices 138 can be used to display a user interface, which may include various graphical user interface (GUI) features that are usable to perform inspection operations, and/or to create and/or modify part programs, to view the images captured by the camera system 260, and/or to directly control the vision system components portion 200.

In various exemplary embodiments, when a user utilizes the machine vision inspection system 100 to create a part program for the workpiece 20, the user generates part program instructions either by explicitly coding the instructions automatically, semi-automatically, or manually, using a workpiece programming language, and/or by generating the instructions by operating the machine vision inspection system 100 in a learn mode to provide a desired image acquisition training sequence. For example, a training sequence may comprise positioning a workpiece feature in the field of view (FOV), setting light levels, focusing or autofocusing, acquiring an image, and providing an inspection training sequence applied to the image (e.g., using video tools). The learn mode operates such that the sequence(s) are captured or recorded and converted to corresponding part program instructions. These instructions, when the part program is executed, will cause the machine vision inspection system to reproduce the trained image acquisition and inspection operations to automatically inspect a workpiece or workpieces matching the workpiece used when creating the part program.

These analysis and inspection methods that are used to inspect features in a workpiece image are typically embodied in various video tools included in the video tool portion 143 of the memory 140. Many known video tools, or "tools" for short, are included in commercially available machine vision inspection systems, such as the QUICK VISION® series of vision systems and the associated QVPAK® software, discussed above.

Figure 3:
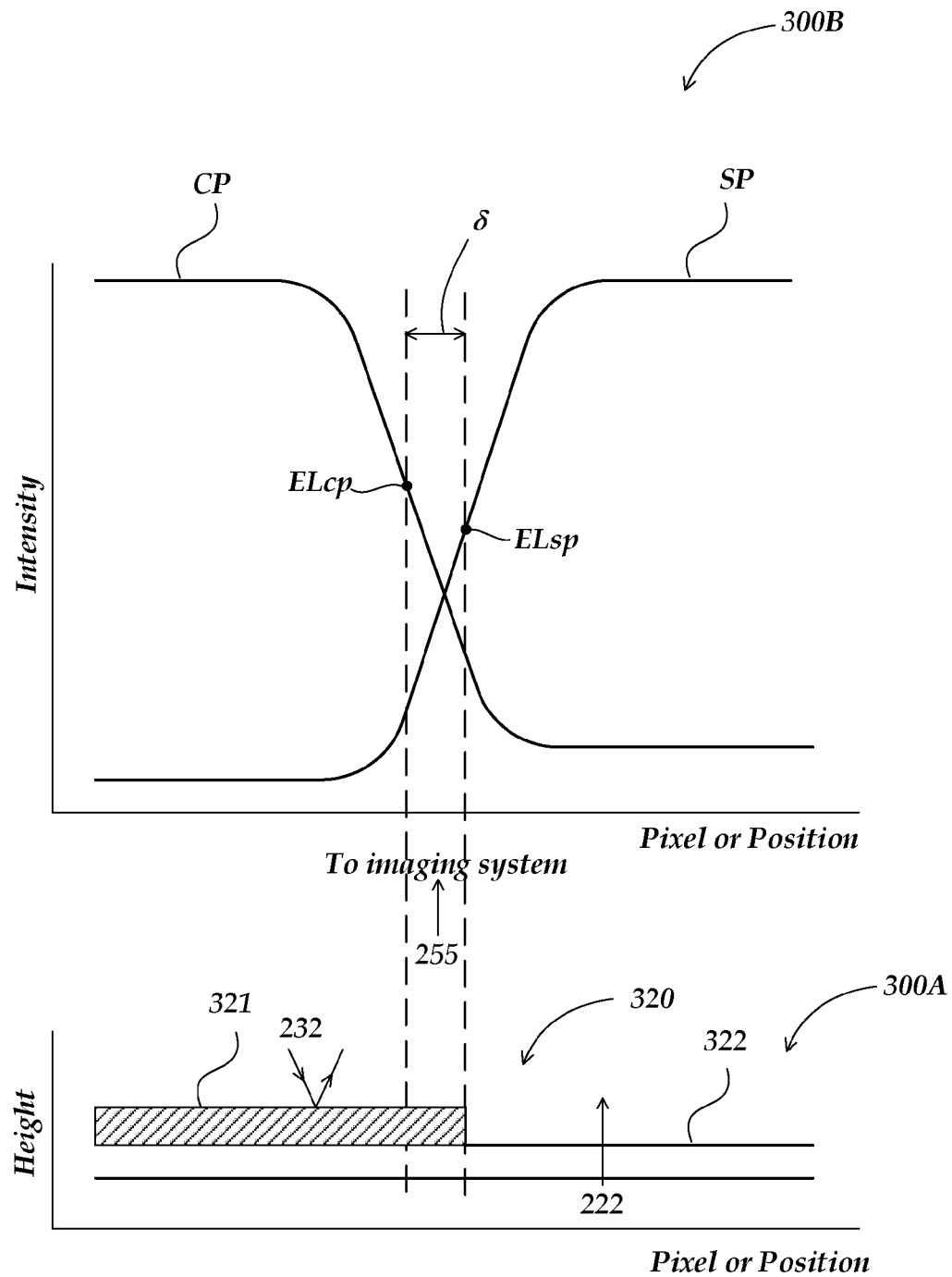
FIG. 3 shows a cross section view of features on a representative workpiece aligned with signal intensity profiles along a scan line of a workpiece edge feature.

FIG. 3 shows a cross section view 300A of features on a representative workpiece aligned with a corresponding set of signal intensity profiles 300B along a scan line in images of a workpiece edge feature 320 associated with edge location operations. The set of signal intensity profiles 300B depict a difference between an edge location ELsp detected in stage light image, and an edge location ELcp detected in coaxial light image, as described in greater detail below.

The workpiece edge feature 320 comprises an opaque portion 321 that reflects coaxial source light 232 toward the imaging system and blocks stage source light 222, and a transmissive portion 322 (e.g., a transparent substrate, a bore or simply a region beyond an edge where workpiece material is absent) that transmits stage source light 222 toward the imaging system. In other words, coaxial light is the main contributor to the workpiece light 255 that forms the image of the opaque portion 321, and stage light is the main contributor to the workpiece light 255 that forms the image of the transmissive portion 322. The set of signal intensity profiles 300B shows a coaxial light image profile CP and a stage light image profile SP. The coaxial light image profile CP corresponds to an edge detection scan line (e.g., along a line of image detector pixels) when the workpiece edge feature 320 is illuminated with the coaxial light 232 from the coaxial light 230 to form a coaxial light image of the edge feature 320. The stage light image profile SP corresponds to an edge detection scan line when the workpiece edge feature 320 is illuminated with the stage light 222 from the stage light 220 to form a stage light image of the edge feature 320.

The coaxial light image profile CP indicates an edge location ELcp that is determined based on the data of the coaxial light image profile CP (e.g., as determined by applying a known type of edge detection algorithm, such as a maximum gradient edge detector that is used in the video tools of the machine vision inspection system.) Similarly, the stage light image profile SP indicates an edge location ELsp that is determined based on the data of the stage light image profile SP (e.g., as determined by applying a known type of edge detection algorithm that is used in the video tools of the machine vision inspection system). There is a difference 8 equal to (ELsp-ELcp) between the detected edge locations, described below.

Illumination-dependent edge location errors at the sub-pixel and/or sub-micron level may be difficult to detect and/or characterize. Prior art methods have used precision reference objects to determine offset error correction factors. However, since the fabrication tolerances and/or thermal expansion of reference objects may be of the same order as such illumination-dependent edge location errors, such prior methods are undesirable for their use of reference objects as well as for their complexity, which is beyond the skill of many users of machine vision inspection systems. Furthermore, some prior art methods may not be applicable to reduce sub-pixel level errors, due to lack of consideration of the limited detector resolution.

The inventors have found that stage light systems may provide images that yield accurate edge location results (e.g., within the fabrication uncertainty of precision reference objects). Stage light systems that collimate light from a light generator to illuminate a workpiece image may provide particularly accurate edge locations and may exhibit relatively low variation between workpieces. In some embodiments, stage light systems that also pass the collimated light through a diffuser plate may similarly provide accurate edge locations. It will be appreciated that for various types of workpieces, the light that forms a stage light "shadow" image is generally not reflected from a surface, or an edge radius, or the like. Therefore, stage light images may be relatively unaffected by material and edge profile variations that affect reflected light images. Methods disclosed herein measure an edge using the stage light and use that measurement as an accurate reference measurement. That same edge may be measured using the coaxial light, and the difference in the edge location (the difference 8, outlined above) may be stored and used as a coaxial light edge position correction factor. In some embodiments, it is preferable that the edge not be moved between the acquisition of images which are used to determine the difference, in order to eliminate errors due to detector and/or optical imperfections and/or motion system measurement errors. The inventors have found that coaxial light images may exhibit edge location errors that are as much as ten times larger than location measurement errors using stage light images. Determining and applying a coaxial light edge position correction factor as disclosed herein has been shown to reduce coaxial light edge location errors by approximately two to five times, or more, for a variety of applications.

It should be appreciated that a coaxial light edge position correction factor has a particular polarity; that is, the offset error is either toward the brighter side of an edge or the darker side of an edge. For many edges the coaxial light image produces an apparent location of the edge which includes an offset error toward the brighter side of the edge. Thus, in such cases, the coaxial light edge position correction factor is applied to correct the edge location to be farther toward the darker side of the edge. For this reason, in some embodiments, the coaxial light edge position correction factor comprises both a magnitude and a polarity such that it may be applied globally, and the operations of the illumination-dependent correction mode portion may include determining the polarity of the edge in the image and applying the correction factor to correct the edge location with the proper polarity relative to the image. In various embodiments, the coaxial light edge position correction factor is also determined and applied along a direction that is perpendicular to an edge.

Figure 4:
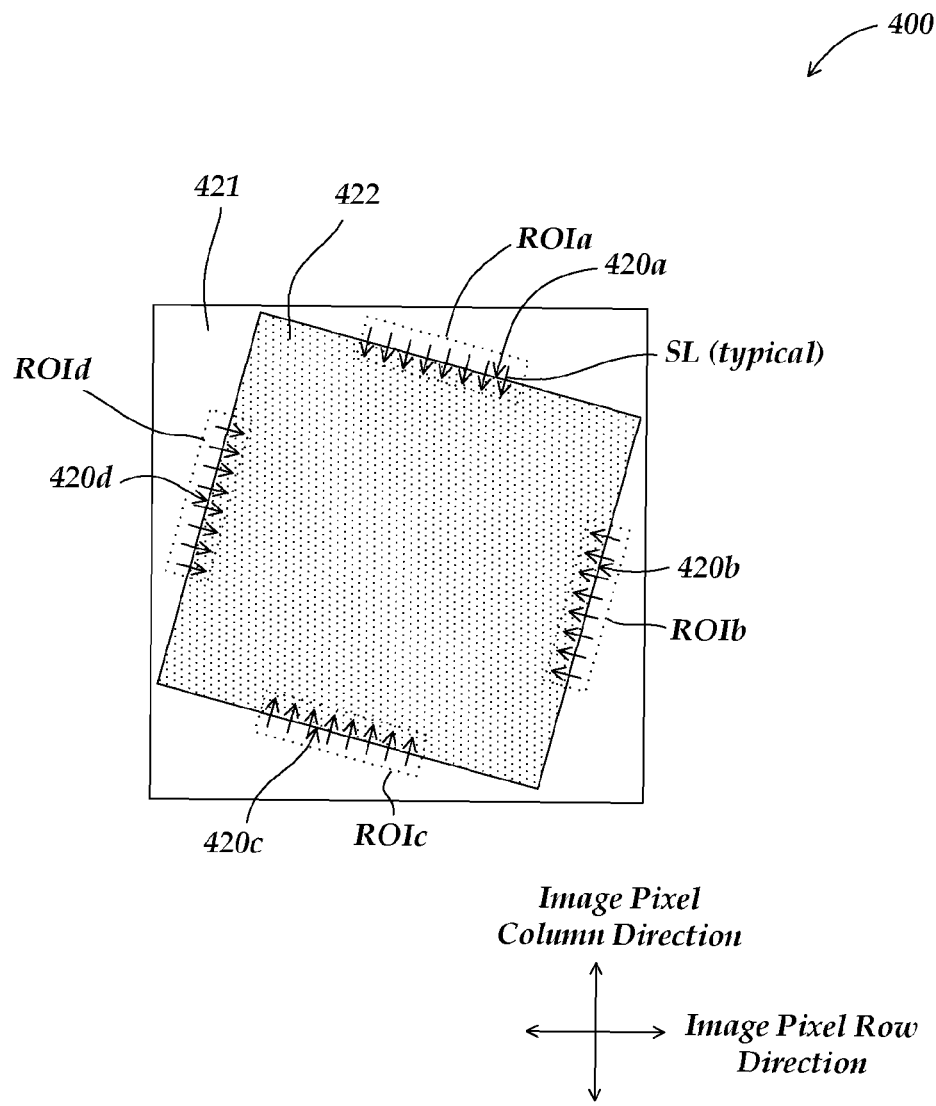
FIG. 4 shows a field of view of a machine vision inspection system which includes features of a representative workpiece.

As previously indicated, to reduce sub-pixel level offset errors, consideration of the limited detector resolution may be required. FIG. 4 shows a field of view 400 of a machine vision inspection system which includes a workpiece including edge features 420a-420d which have a configuration which may be advantageous for determining a coaxial light edge position correction factor with very high accuracy.

The field of view 400 includes a square opaque portion 421 and a transmissive portion 422, which may operate as previously described for the opaque portion 321 and transmissive portion 322 of FIG. 3. The square shape is exemplary and not limiting. The illustrated regions of interest ROIa, ROIb, ROIc, and ROId are associated with respective edge location video tools 143ed which are configured to measure various edge features 420a-420d. A first instance of the video tools may measure their respective edges using a stage light image, and a second instance of the video tools may measure their respective edges using a coaxial light image. In some cases, it is advantageous to measure the difference of an edge location using coaxial and stage light a plurality of times, and/or at a plurality of locations to determine a coaxial light edge position correction factor based on an average value that is less likely to include local or temporary sources of measurement noise arising from irregularities in the optics or detector or vibration or the like.

In addition, it will be appreciated that the edges in the regions of interest ROIa-ROId are rotated with respect to the row and column directions of the detector. Thus, the various scan lines SL sample the signal intensity profile with a different relationship between the edge and the pixels along each scan line. The edge location is determined from the plurality of scan lines in the ROI. In effect, this is substantially similar to sampling the edge signal intensity profile with a higher density sampling than the detector pixel spacing and allows the edge position to be determined with higher resolution. This may be important when attempting to correct sub-pixel offset errors.

In addition, if the square opaque portion 421 is an object having a known dimension, the distance between stage light measurements of the opposing sides of the square may be compared to the known dimension of the square to verify that the stage light measurements have a negligible offset error, if desired.

Figure 5:
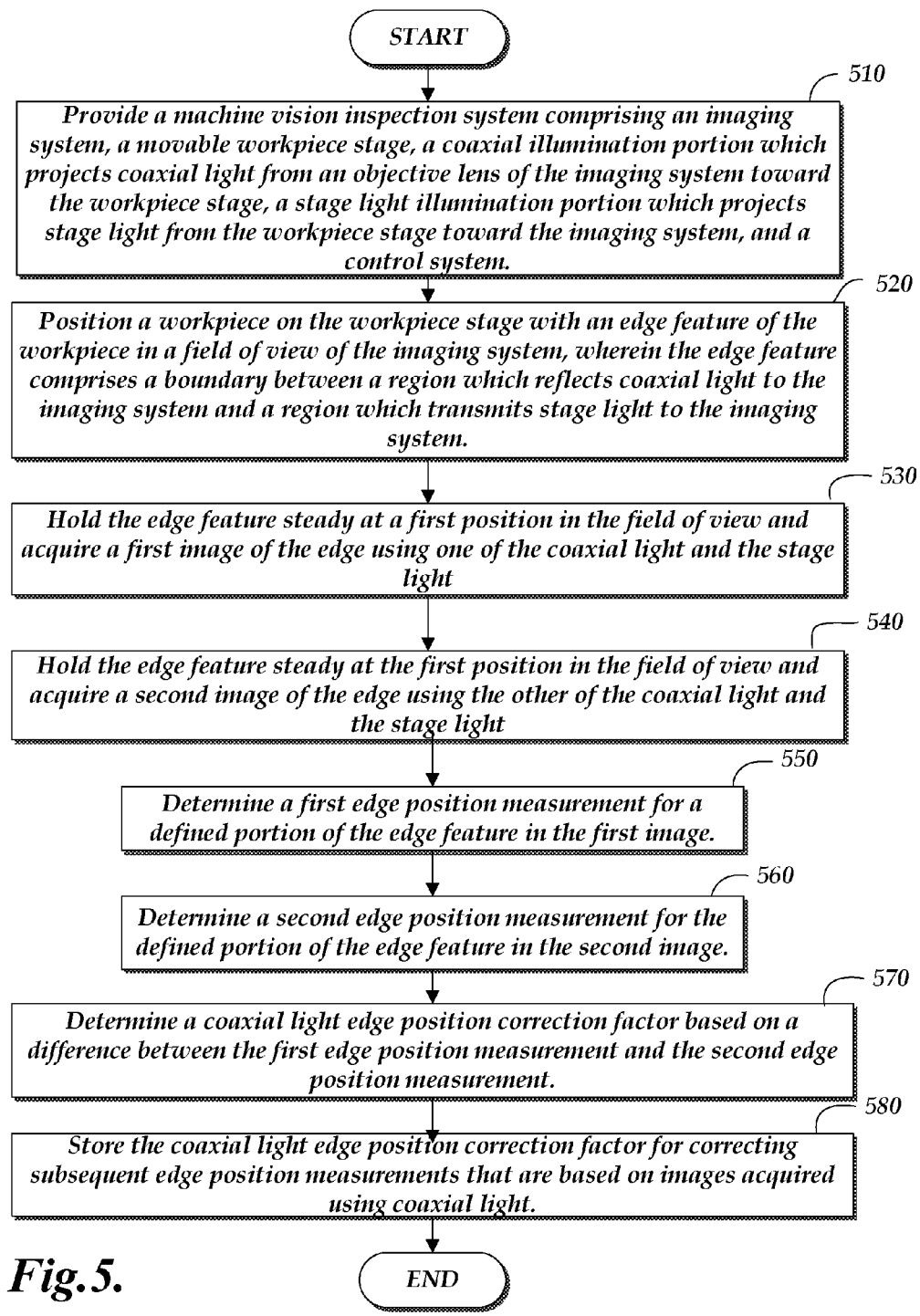
FIG. 5 is a flow diagram outlining a method and routine for operating a machine vision inspection system to determine a correction factor used to provide illumination-dependent corrections for subsequent edge location measurements.

FIG. 5 is a flow diagram 500 outlining a method and routine for operating a machine vision inspection system to determine a coaxial light edge position correction factor used to provide illumination-dependent corrections for subsequent edge location measurements.

At a block 510, a machine vision inspection system is provided, which comprises an imaging system (e.g., the optical assembly portion 205), a workpiece stage (e.g., the workpiece stage 210), a coaxial illumination portion (e.g., coaxial light 230) which projects coaxial light (e.g., the coaxial source light 232) from an objective lens (e.g., the objective lens 250) of the imaging system toward the workpiece stage, a stage light illumination portion (e.g., the stage light 220) which projects stage light (e.g., the stage source light 222) from the workpiece stage toward the imaging system, and a control system (e.g., the control system portion 120).

At a block 520, a workpiece (e.g., the workpiece 20) is positioned on the workpiece stage with an edge feature of the workpiece (e.g., the edge feature 320 or 420) in a field of view (e.g., the field of view 400) of the imaging system, wherein the edge feature comprises a boundary between a region which reflects coaxial light (e.g., the opaque portion 321 or 421) to the imaging system and a region which transmits stage light (e.g., the reflective portion 322 or 422) to the imaging system.

At a block 530, the edge feature is held steady at a first position in the field of view and a first image of the edge is acquired using one of the coaxial light and the stage light.

At a block 540, the edge feature is held steady at the first position in the field of view and a second image of the edge is acquired using the other of the coaxial light and the stage light.

At a block 550, a first edge position measurement is determined for a defined portion of the edge feature in the first image. For example, the first edge position measurement may be determined based on analysis of a first one of the coaxial light image profile CP or the stage light image profile SP, or a plurality of such profiles at respective scan lines across the edge in the first image.

At a block 560, a second edge position measurement is determined for the defined portion of the edge feature in the second image. For example, the second edge position measurement may be determined based on analysis of the other of the coaxial light image profile CP or the stage light image profile SP, or a plurality of such profiles at respective scan lines across the edge in the first image.

At a block 570, a coaxial light edge position correction factor is determined based on a difference between the first edge position measurement and the second edge position measurement (e.g., based on the difference 6).

At a block 580, the coaxial light edge position correction factor is stored for correcting subsequent edge position measurements that are based on images acquired using coaxial light. In the exemplary embodiment of FIG. 2, the coaxial light edge position correction factor is stored in the illumination correction factor portion 140cf of the memory 140.

In some embodiments or applications, the edge position correction factor may be used for adjusting a measurement determined in an analogous manner to that of the block 550 or 560 using coaxial light. In such a case the method may comprise additional steps of: acquiring a subsequent image of an edge feature using the coaxial light, determining an edge position measurement for the edge feature in the subsequent image, and correcting that edge position measurement by adjusting it based on the coaxial light edge position correction factor. The steps may be implemented via the illumination-dependent correction mode portion 143idc of FIG. 2.

In some embodiments, the method and routine shown in the flow diagram 500 comprises performing the steps at blocks 510 through 560 repeatedly for an edge, or for a plurality of edges and/or different edge orientations, and then at the block 570 the coaxial light edge position correction factor is determined based on the resulting plurality of respective first and second edge position measurements, for example, based on an average of the differences of the resulting respective first and second edge position measurements, or as previously outlined with reference to FIG. 4.

In some embodiments, or in some part programs, a coaxial light edge position correction factor is determined based on a desired workpiece (e.g., a calibration object or a standard workpiece) and is applied globally. That is, it is used to correct coaxial light image edge locations measured during run mode operations on various workpieces and/or edges.

In some embodiments, or when creating certain part programs, a coaxial light edge position correction factor may be determined for a particular representative workpiece during learn mode (e.g., using the method and routine shown in the flow diagram 500) and applied globally for coaxial images of that workpiece during run mode operations on similar workpieces. In another case, in some embodiments, or when creating certain part programs, a coaxial light edge position correction factor may be determined for a particular edge configuration on a representative workpiece during learn mode and applied only to coaxial images of that particular edge configuration during run mode operations on similar workpieces. Compared to stage light images, the edge location in coaxial light images is more sensitive to the particular materials and configuration of an edge (e.g., including its thickness, surface finish, shape, and the like). Therefore, it will be appreciated that applying a coaxial light edge position correction factor globally in machine vision inspection system may reduce coaxial image edge location errors to a first degree. A further degree of error reduction may be achieved with a part program that performs run mode operations that include applying a workpiece-specific coaxial light edge position correction factor that is determined during learn mode operations using a representative workpiece. A further degree of error reduction may be achieved with a part program that performs run mode operations that include applying an edge-specific coaxial light edge position correction factor (e.g., for a specific instance of a video tool on a specific edge) that is determined during learn mode operations for that specific edge and/or video tool instance on a representative workpiece.

In some embodiments, the method(s) disclosed herein for correcting coaxial light image edge locations based on a coaxial light edge position correction factor may be applied (or not applied) based on a user selection in a graphical user interface (GUI) of the machine vision inspection system. The GUI may be implemented using the control system of the machine vision inspection system. In some embodiments, the GUI may include an illumination-dependent correction selector (e.g., a check box or radio button) included in a video tool parameter listing/editing box included in the GUI. The GUI may include a global illumination-dependent correction selector (e.g., a check box in default listing/editing box) that determines whether the correction method will be globally applied to edge detection in all coaxial light images within a part program, and/or a tool-specific illumination-dependent correction selector (e.g., a check box in tool parameter listing/editing box for a particular instance of a video tool applied to a coaxial light image) that determines whether the correction method will be applied to edge detection in that particular instance of the video tool within a part program. In some embodiments, respective coaxial light edge position correction factors may be determined for different types of edge features (e.g., a thick copper edge, a thin gold edge, a thin chrome edge, etc.) and the GUI may include a selector or selectors that allows a user to select a particular one of the respective correction factors to be implemented for a particular workpiece or a particular instance of a video tool.

While various preferred and exemplary embodiments of the invention have been illustrated and described, it will be appreciated that various changes can be made therein without departing from the spirit and scope of the invention.

The invention claimed is:

1. A method for correcting coaxial light edge position skewing in operations of a machine vision inspection system which comprises an imaging system, a movable workpiece stage, a coaxial illumination portion which projects coaxial light from an objective lens of the imaging system toward the workpiece stage, a stage light illumination portion which projects stage light from the workpiece stage toward the imaging system, and a control system, the method comprising:
   (a) positioning a workpiece on the workpiece stage with an edge feature of the workpiece in a field of view of the imaging system, wherein the edge feature comprises a boundary between a region which reflects coaxial light to the imaging system and a region which transmits stage light to the imaging system;
   (b) holding the edge feature steady at a first position in the field of view and acquiring a first image of the edge using one of the coaxial light and the stage light;
   (c) holding the edge feature steady at the first position in the field of view and acquiring a second image of the edge using the other of the coaxial light and the stage light;
   (d) determining a first edge position measurement for a defined portion of the edge feature in the first image;
   (e) determining a second edge position measurement for the defined portion of the edge feature in the second image;
   (f) determining a coaxial light edge position correction factor based on a difference between the first edge position measurement and the second edge position measurement; and
   (g) storing the coaxial light edge position correction factor for correcting subsequent edge position measurements that are based on images acquired using coaxial light.

2. The method of claim 1, further comprising performing the steps (a) through (e) a plurality of times, wherein the edge position correction factor is determined in step (f) based on the resulting plurality of first and second edge position measurements.

3. The method of claim 2, wherein the steps (a) through (e) are performed for a plurality of different edges.

4. The method of claim 1, further comprising:
   (h) acquiring a subsequent image of an edge feature of a workpiece using the coaxial light;
   (i) determining an edge position measurement for the edge feature in the subsequent image; and
   (j) correcting that edge position measurement by adjusting it based on the coaxial light edge position correction factor.

5. The method of claim 4, wherein the operations of steps (h), (i), and (j) are performed by operations of an edge detection video tool which includes illumination-dependent edge location correction operations.

6. The method of claim 5, wherein:
the steps (a) through (g) are performed for a particular representative workpiece during learn mode operations of the machine vision inspection system;
the operations of steps (h) through (j) are recorded in a part program based on training associated with an edge detection video tool which includes illumination dependent edge location correction operations, wherein the training is performed using that particular representative workpiece during the learn mode operations; and
the operations of steps (h), (i), and (j) are performed by executing the part program for a workpiece similar to the representative workpiece during run mode operations of the machine vision inspection system.

7. The method of claim 6, wherein:
the steps (a) through (g) are performed for a particular edge on the representative workpiece during learn mode operations of the machine vision inspection system;
the operations of steps (h) through (j) are recorded in a part program based on training associated with an edge detection video tool which includes an illumination-dependent edge location correction operations, wherein the training is performed using that particular edge on the representative workpiece during the learn mode operations; and
the operations of steps (h), (i), and (j) are performed by executing the part program for a workpiece similar to the representative workpiece during run mode operations of the machine vision inspection system.

8. The method of claim 5, wherein the edge detection video tool which includes illumination-dependent edge location correction operations comprises a graphical user interface including an illumination-dependent correction selector which determines whether or not step (j) is performed, and the method comprises a user of the machine vision inspection system setting the illumination-dependent correction selector such that step (j) is performed.

9. The method of claim 1, wherein:
the steps (a) through (g) are performed for a first type of edge feature and the steps (a) through (g) are performed for at least a second type of edge feature, such that at least two respective coaxial light coaxial light edge position correction factors are stored; and
the method further comprises using an edge detection video tool which includes illumination-dependent edge location correction operations to perform the steps:
 (h) acquiring a subsequent image of an edge feature of a workpiece using the coaxial light;
 (i) determining an edge position measurement for the edge feature in the subsequent image; and
 (j) correcting that edge position measurement by adjusting it based on a coaxial light edge position correction factor,
wherein the machine vision inspection system comprises a graphical user interface including a selection feature that allows a user to select which of the respective coaxial light edge position correction factors is applied in step (j) and the method comprises a user of the machine vision inspection system operating that selection feature.

10. The method of claim 1, wherein the stage light illumination portion comprises a light generator and collimating optics that output collimated light.

11. The method of claim 10, wherein the stage light illumination portion comprises an output light diffuser that inputs the collimated light and outputs stage source light that is at least partially diffuse.

* * * * *

UNITED STATES PATENT AND TRADEMARK OFFICE
CERTIFICATE OF CORRECTION

PATENT NO. : 8,280,172 B1  
APPLICATION NO. : 13/053880  
DATED : October 2, 2012  
INVENTOR(S) : S. R. Campbell et al.

Page 1 of 1

It is certified that error appears in the above-identified patent and that said Letters Patent is hereby corrected as shown below:

On the Title Page

Column 1, Prior Publication Data, below Item "(22) Filed: Mar. 22, 2011" insert
-- (65) Prior Publication Data
US 2012/0243790 A1 Sept. 27, 2012 --

Signed and Sealed this
First Day of October, 2013

Teresa Stanek Rea
*Deputy Director of the United States Patent and Trademark Office*